United States Patent
Vad

(10) Patent No.: US 9,827,121 B2
(45) Date of Patent: Nov. 28, 2017

(54) QUICK RELEASE DEPLOYMENT HANDLE FOR MEDICAL DEVICES

(71) Applicant: Cook Medical Technologies LLC, Bloomington, IN (US)

(72) Inventor: Siddharth Vad, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 54 days.

(21) Appl. No.: 14/206,799

(22) Filed: Mar. 12, 2014

(65) Prior Publication Data

US 2014/0277349 A1 Sep. 18, 2014

Related U.S. Application Data

(60) Provisional application No. 61/801,469, filed on Mar. 15, 2013.

(51) Int. Cl.
*A61F 2/95* (2013.01)
*A61F 2/962* (2013.01)
*A61F 2/966* (2013.01)

(52) U.S. Cl.
CPC .............. *A61F 2/95* (2013.01); *A61F 2/962* (2013.01); *A61F 2/966* (2013.01); *A61F 2002/9511* (2013.01); *A61F 2002/9517* (2013.01); *A61F 2002/9665* (2013.01)

(58) Field of Classification Search
CPC .... A61F 2/95; A61F 2/962; A61F 2002/9517; A61F 2/966; A61F 2002/9665; A61F 2002/9511

See application file for complete search history.

(56) References Cited

U.S. PATENT DOCUMENTS

| | | | |
|---|---|---|---|
| 5,776,142 A * | 7/1998 | Gunderson | A61F 2/88 606/108 |
| 5,944,727 A | 8/1999 | Ahari et al. | |
| 6,572,648 B1 * | 6/2003 | Klumb | A61F 2/88 623/1.15 |
| 7,604,640 B2 * | 10/2009 | Kana | A61B 17/8875 173/1 |
| 2001/0027323 A1 | 10/2001 | Sullivan et al. | |
| 2002/0091439 A1 | 7/2002 | Baker et al. | |
| 2002/0151956 A1 * | 10/2002 | Chobotov | A61F 2/07 623/1.12 |
| 2003/0009175 A1 * | 1/2003 | Cassidy, Jr. | A61B 17/3421 606/108 |

(Continued)

FOREIGN PATENT DOCUMENTS

EP 2777653 A1 9/2014

OTHER PUBLICATIONS

Examination Report for corresponding EP Application No. 14275071.0 dated Jul. 3, 2017, 6 pages.

(Continued)

*Primary Examiner* — Jiang Ou
(74) *Attorney, Agent, or Firm* — Brinks Gilson & Lione

(57) ABSTRACT

A deployment handle for an expandable medical device, a handle having a proximal end, a distal end, and a lumen/passageway extending between the proximal and distal ends; an inner cannula; and a tension mechanism located inside the handle and secured to the inner cannula so that the inner cannula rotates when the tension mechanism is actuated.

14 Claims, 6 Drawing Sheets

(56) References Cited

U.S. PATENT DOCUMENTS

| | | | |
|---|---|---|---|
| 2004/0006380 A1* | 1/2004 | Buck | A61F 2/966 623/1.11 |
| 2005/0149159 A1* | 7/2005 | Andreas | A61F 2/95 623/1.11 |
| 2005/0149160 A1 | 7/2005 | McFerran | |
| 2006/0136034 A1* | 6/2006 | Modesitt | A61F 2/88 623/1.11 |
| 2006/0136035 A1 | 6/2006 | Hermann et al. | |
| 2006/0265045 A1 | 11/2006 | Shiu et al. | |
| 2006/0271153 A1* | 11/2006 | Garcia | A61B 17/12022 623/1.11 |
| 2007/0203503 A1 | 8/2007 | Salahieh et al. | |
| 2007/0260301 A1* | 11/2007 | Chuter | A61F 2/95 623/1.11 |
| 2008/0082158 A1 | 4/2008 | Tseng et al. | |
| 2008/0208320 A1 | 8/2008 | Tan-Malecki et al. | |
| 2008/0281353 A1* | 11/2008 | Aranyi | A61B 17/064 606/219 |
| 2009/0105798 A1 | 4/2009 | Koch | |
| 2009/0143738 A1 | 6/2009 | Hendriksen et al. | |
| 2009/0240262 A1 | 9/2009 | Shifrin et al. | |
| 2010/0094393 A1* | 4/2010 | Cordeiro | A61F 2/95 623/1.11 |
| 2011/0054585 A1* | 3/2011 | Osborne | A61F 2/95 623/1.11 |
| 2011/0251664 A1 | 10/2011 | Acosta de Acevedo | |
| 2011/0257719 A1 | 10/2011 | Argentine | |
| 2011/0282425 A1 | 11/2011 | Dwork | |
| 2011/0288558 A1* | 11/2011 | Nimgaard | A61F 2/95 606/108 |
| 2012/0158115 A9 | 6/2012 | Arnault de la Menardiere et al. | |
| 2012/0221091 A1 | 8/2012 | Hartly et al. | |
| 2013/0131775 A1 | 5/2013 | Hadley et al. | |
| 2013/0338787 A1 | 12/2013 | Hopkins et al. | |

OTHER PUBLICATIONS

Examination Report for corresponding EP Application No. 14275071.0 dated Jan. 18, 2017, 6 pages.

* cited by examiner

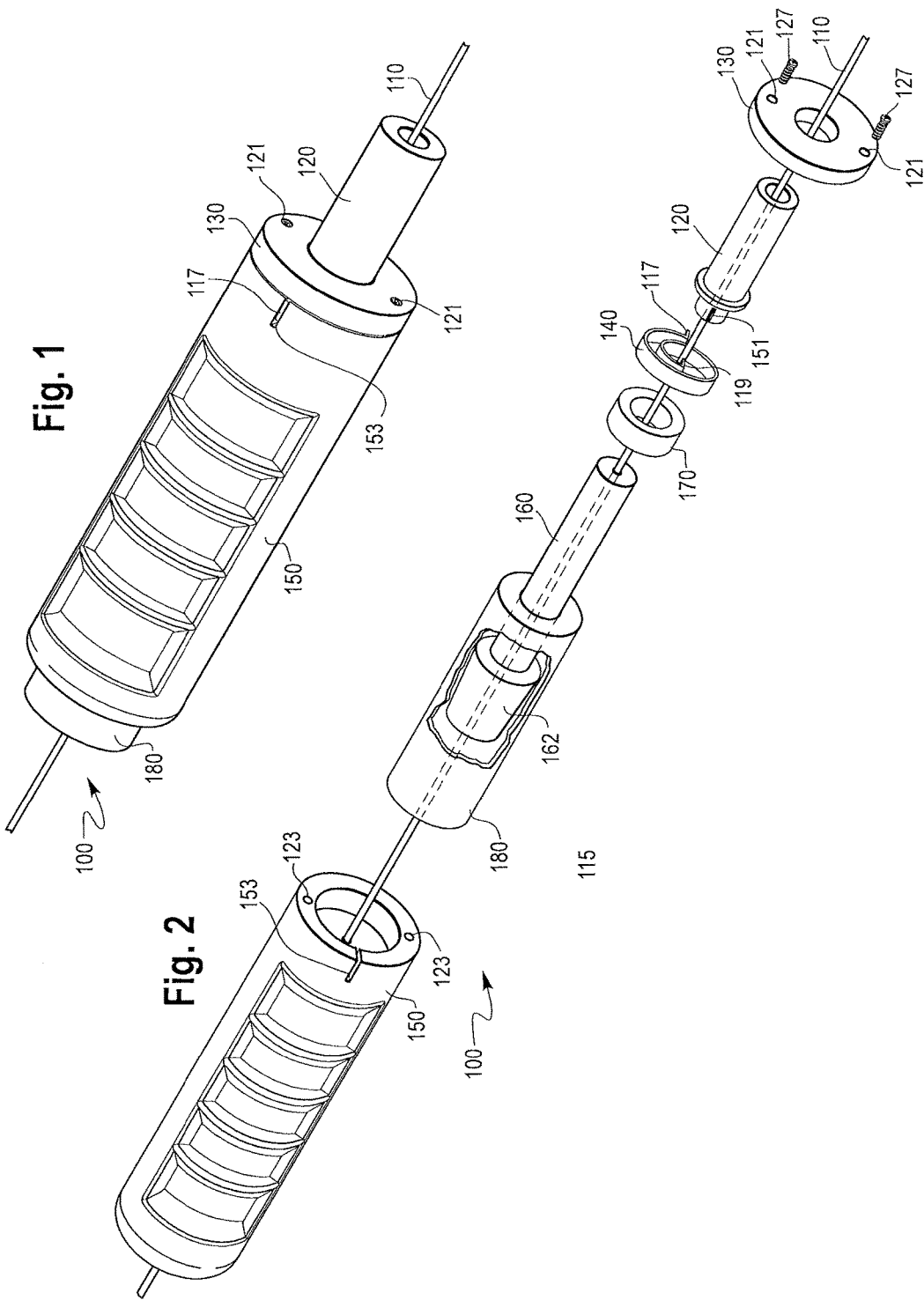

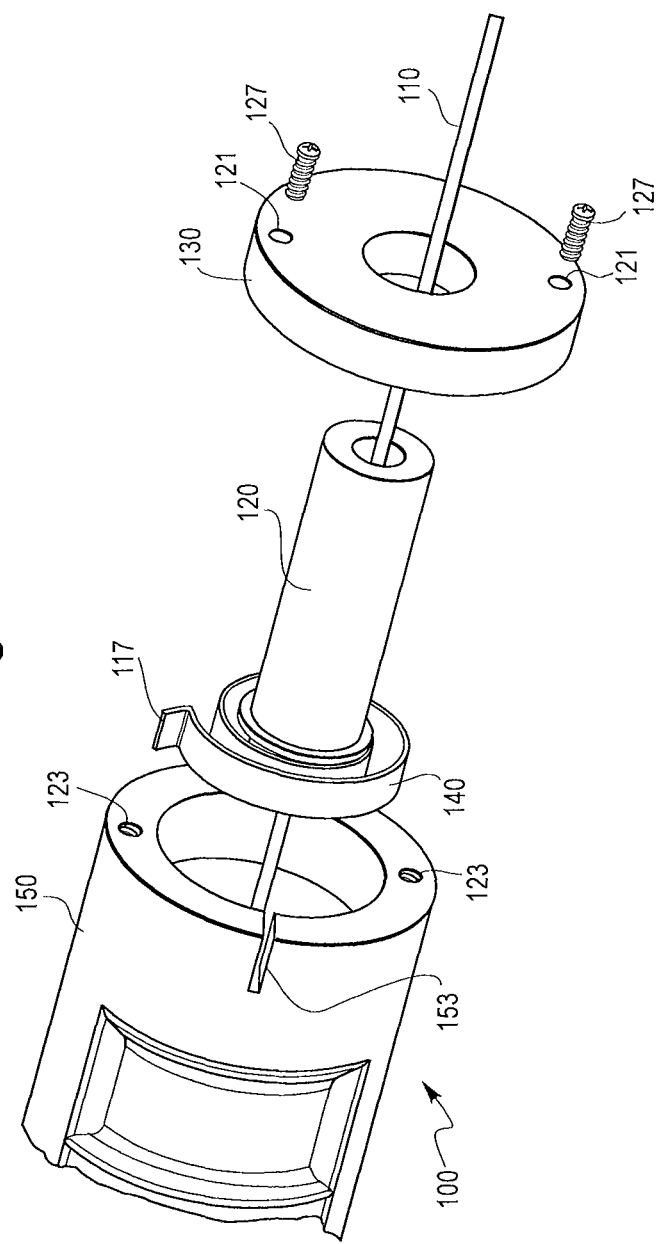

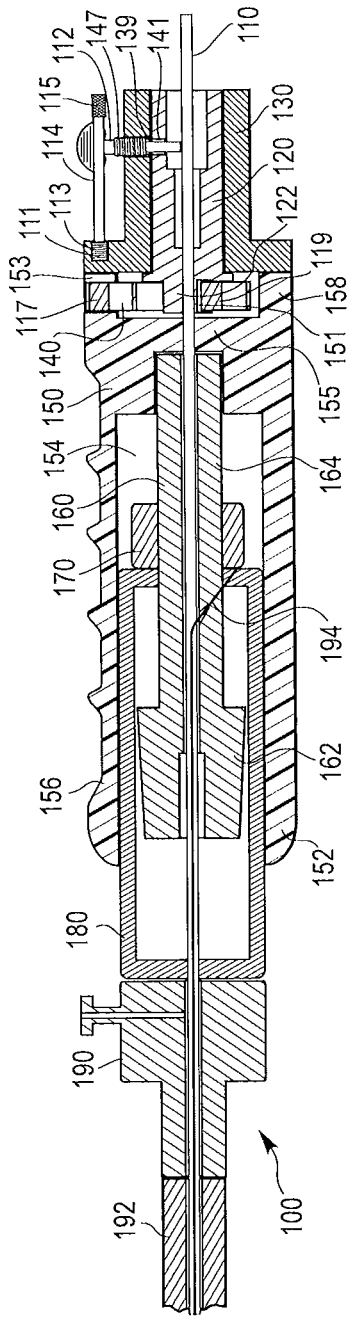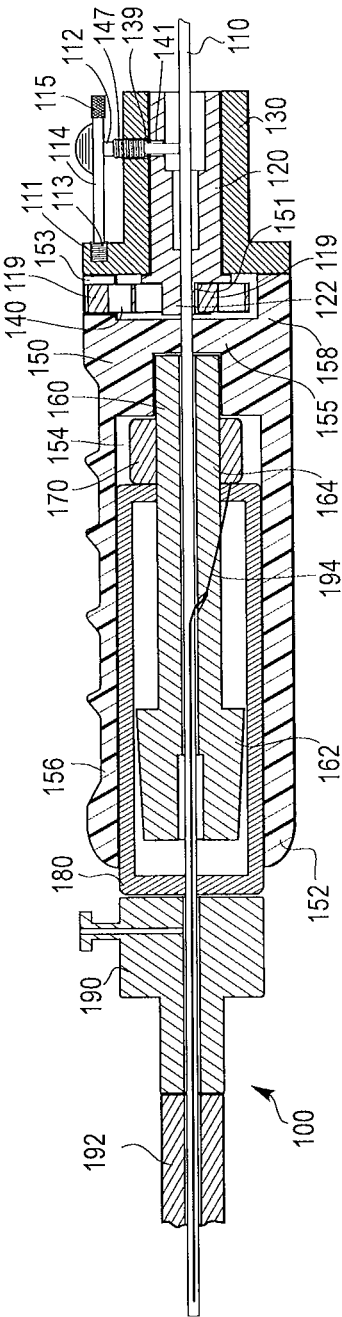

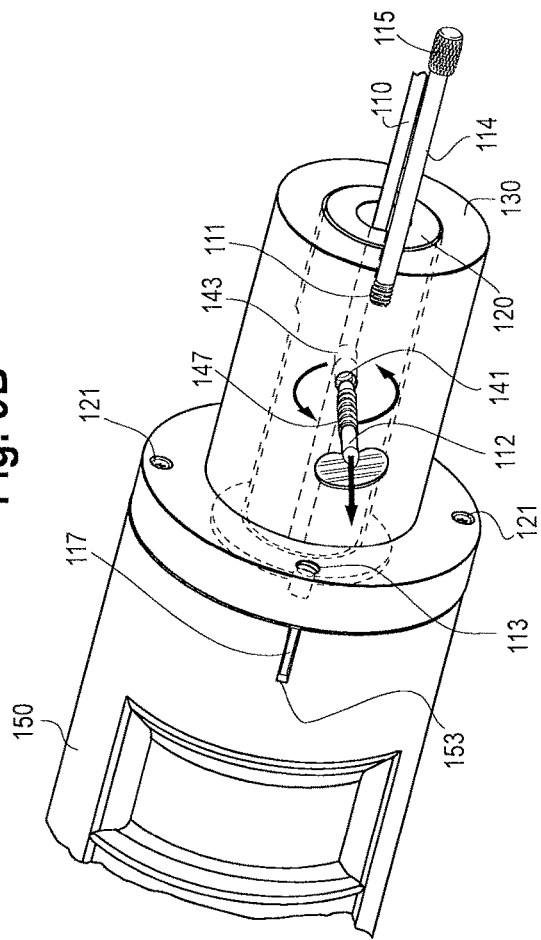
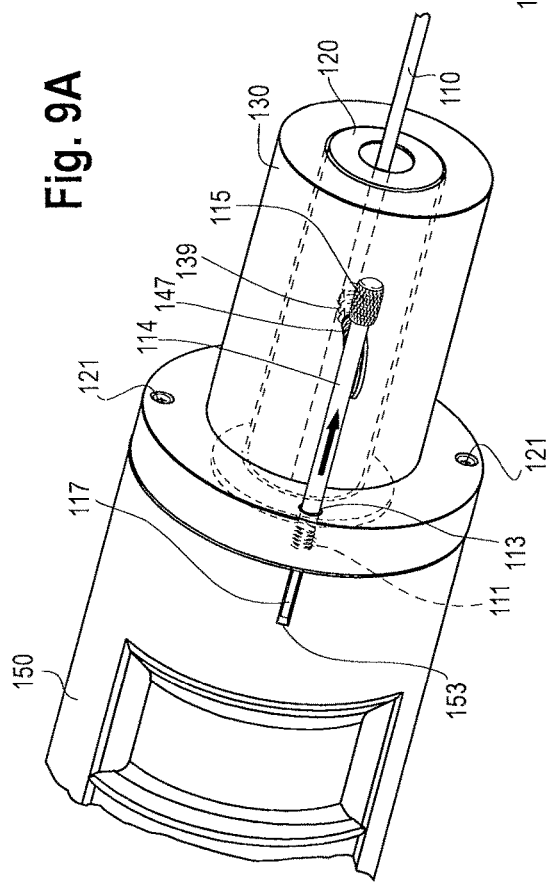

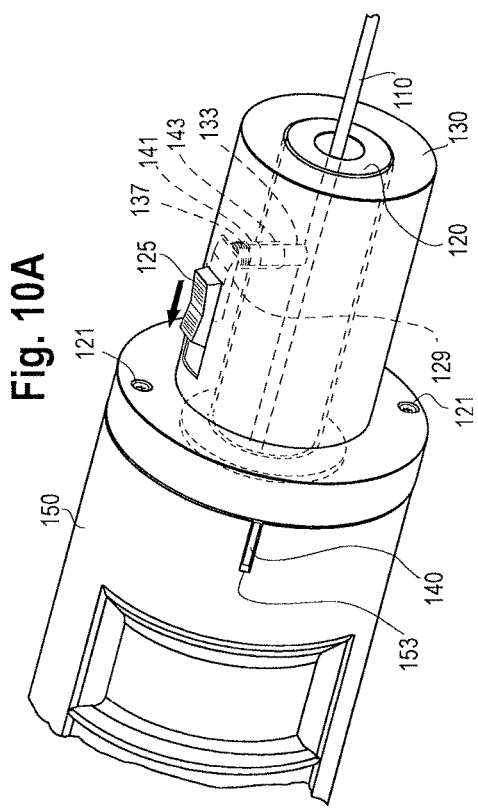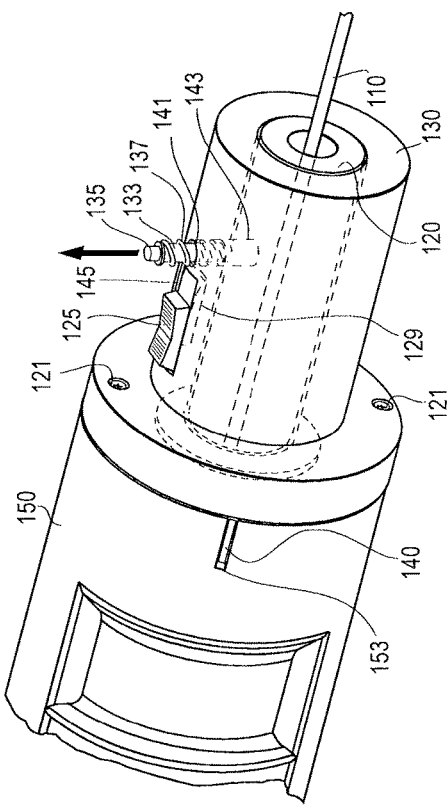

QUICK RELEASE DEPLOYMENT HANDLE FOR MEDICAL DEVICES

RELATED APPLICATIONS

The present patent document claims the benefit of the filing date under 35 U.S.C. §119(e) of Provisional U.S. Patent Application Ser. No. 61/801,469, filed Mar. 15, 2013, which is hereby incorporated by reference.

TECHNICAL FIELD

This invention relates to medical devices for introduction into a patient. Particularly, this invention relates to a medical device delivery system for delivering a prosthesis to an implant site of a patient through an introducer/delivery device.

BACKGROUND

A vascular aneurysm is the result of abnormal dilation of a blood vessel resulting from disease or a genetic condition that causes the arterial wall to weaken and expand. While aneurysms can potentially occur in any blood vessel, aneurysms occur predominantly in the aorta and peripheral arteries.

In the past, aortic aneurysms were commonly treated using open surgical procedures that, while effective, were often significantly life-threatening. Therefore, less invasive techniques were developed. One of these techniques involved the use of a catheter based delivery system that delivers an aortic graft to a target site at which the graft is to be deployed within the aorta.

In a catheter based delivery system, a less invasive entry point is used to introduce the aortic graft. The aortic graft is then advanced through the blood vessel to the site where the prosthesis is to be deployed (i.e. the aorta). An exemplary delivery system includes a delivery catheter with an inner tube (positioner) and an outer tube (sheath). The sheath is capable of axial movement. The aortic graft is attached to a flexible rod (cannula) and compressed within the sheath in front of the positioner. The delivery catheter is then maneuvered until the proximal end of the catheter containing the aortic graft is positioned in the vicinity of the target site. There, the positioner is held stationary while the sheath is withdrawn. The positioner serves to prevent the aortic graft from moving backwards as the sheath is withdrawn.

The types of stents that may be used with the aortic graft can be either self-expanding or balloon-expandable. Self-expanding stents may be delivered to a target site in a compressed configuration and subsequently expanded by removing a delivery sheath, trigger wires, or releasing diameter reducing ties. Use of trigger wires has been prevalent in maintaining the position of the aortic graft on the cannula until release.

Past systems have made use of trigger wires to secure the aortic graft at both its proximal and distal end. However, the use of suture loops to maintain the position of the aortic graft on the proximal end of the device has become favored because the threading of trigger wires through the vertices of a stent can often compromise the integrity of the aortic graft. The trigger wire can often become crimped when the stent is compressed within the sheath of the delivery device. If the trigger wires are crimped between the strut segments, the trigger wires and/or stent segments may become damaged during delivery, particularly for nickel-titanium stents that may be sensitive to surface imperfections. Furthermore, when compressing a cannula-cut stent having relatively acute bends to a significantly reduced radial profile, barbs disposed near the apices of the stent may become entangled with the stent struts and/or the trigger wires.

However, the deployment of an aortic graft that is attached to the delivery device by suture loops at the proximal end and trigger wires at the distal end requires a multitude of distinct and careful steps. For example, once the aortic graft is positioned in the vicinity of the target site, the sheath is first withdrawn to expose the proximal end of the cannula and the attached stent. The physician then rotates the cannula to release the top stent from the cannula. The cannula is withdrawn from between the aortic graft and the sheath is then further withdrawn to expose the entirety of the aortic graft. Finally, the trigger wire is withdrawn to release the distal end of the aortic graft and fully deploy the device.

However, because of the various steps necessary to release the aortic graft into the body as well as the high amount of precision needed to accomplish these tasks, physicians prefer to use devices that allow deployment of the prosthesis in the fewest number of steps.

SUMMARY

A deployment handle assembly for a stent graft delivery device is disclosed. In one example, the handle assembly comprises a tubular handle having a proximal end and a distal end and a lumen extending longitudinallytherebetween. An inner cannula has a proximal end and a distal end extend, wherein a stent graft is carried on the proximal end of the inner cannula and at least a portion of the distal end of the inner cannula extends longitudinally through handle lumen. A torsion mechanism configured to impart axial rotation of the inner cannula relative to the handle is located at the distal end of the inner cannula. An actuation mechanism is positioned at the distal end of the handle, the actuation mechanism having a first position in which the actuation mechanism is engaged with inner cannula to prevent axial rotation of the inner cannula and a second position in which the actuation mechanism is disengaged with inner cannula to permit axial rotation of the inner cannula relative to the handle, wherein axial rotation of the inner cannula permits release the stent graft from the delivery device.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

FIG. 1 illustrates one embodiment of a quick release deployment handle of a delivery device.

FIG. 2 illustrates an exploded view of the quick release deployment handle of FIG. 1.

FIG. 3 illustrates an exploded view of the distal end of the quick release deployment handle of FIG. 1.

FIG. 4 illustrates a cross-sectional side view of the quick release deployment handle of FIG. 1 with a sheath of the device withdrawn.

FIG. 5 illustrates a cross-sectional side view of the quick release deployment handle of FIG. 1 with a trigger wire of the delivery device withdrawn.

FIGS. 9A-9B illustrate one embodiment of the distal end of the quick release deployment handle of FIG. 4 with one example of a safety locking mechanism.

FIGS. 10A-10B illustrate another embodiment of the distal end of the quick release deployment handle with an alternative safety locking mechanism.

DETAILED DESCRIPTION

Figure 6:
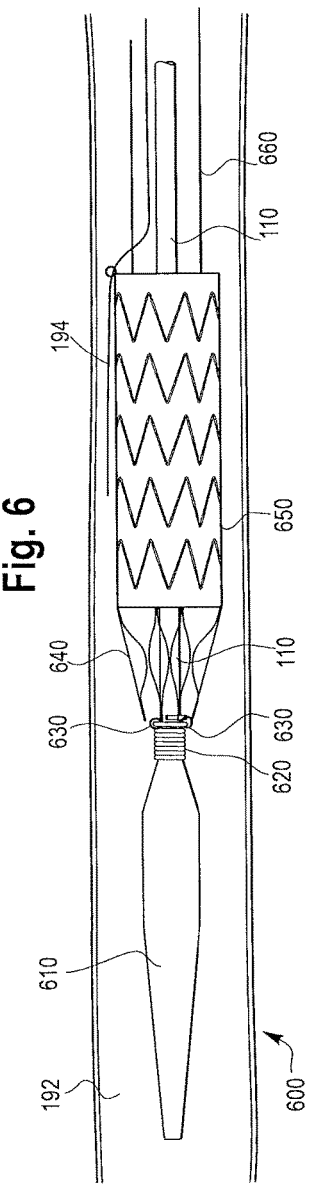
FIG. 6 illustrates a side view of the proximal end of the delivery device of FIG. 1 with a prosthesis loaded thereon.

The embodiments described in this disclosure will be discussed generally in relation to deployment of prostheses, such as stents, grafts and stent grafts into the aorta, but the disclosure is not so limited and may be applied to other vasculature or other body vessels or lumens.

In the present disclosure, the term "proximal" refers to a direction that is generally closest to the heart during a medical procedure, while the term "distal" refers to a direction that is farthest from the heart during a medical procedure.

The term "stent graft" refers to a device that has a tubular body of biocompatible graft material and at least one stent fastened to the tubular body to define a lumen through the stent graft. The stent graft may be bifurcated and/or may include fenestrations, side arms, or the like. Other arrangements of stent grafts are within the scope of this disclosure.

FIGS. 1-5 illustrate one embodiment of a delivery device including a deployment handle 100, which may be configured as a quick release deployment handle. The delivery device includes an inner cannula 110 extending longitudinally along the length of the delivery device. The deployment handle 100 is disposed about the inner cannula 110 near the distal end thereof as further described below. The deployment handle 100 may be configured to cause rotation of the inner cannula 110 relative to the deployment handle to release a stent graft from the delivery device as further described below.

The quick release deployment handle 100 includes a tubular handle 150. The handle 150 has a proximal end 152, a distal end 158, and a lumen 154 extending longitudinally between the proximal end and the distal end of the handle. A divider 155 is positioned longitudinally between the proximal portion 156 and the distal portion 158 of the handle 150 as shown in FIGS. 4-5. The handle 150 has an opening at both the proximal end 152 and the distal end 158. A trigger wire mechanism may be disposed within the distal end 158 as further described below. A tension mechanism may be disposed within the distal portion 158 also as further described below. The divider 155 of the handle 150 may be positioned within the lumen 154 as shown in FIGS. 4-5. In this manner, the divider 155 may divide the lumen 154 into two compartments (e.g., a proximal compartment within the proximal portion 156 and a distal compartment within the distal portion 158). The divider 155 may include an opening extending therethrough so that the proximal compartment and the distal compartment are in communication with one another through the opening in the divider.

As can be seen in FIGS. 4-5, the trigger wire mechanism may include an inner handle 160, a trigger wire knob 170, and a trigger wire pusher 180. The trigger wire pusher 180 may be configured as a tubular member having a proximal end, a distal end, and a lumen extending longitudinally therein. The trigger wire pusher 180 may have an opening at both the proximal end and the distal end thereof. The opening at the distal end of the trigger wire pusher 180 may have a larger diameter than the opening at the proximal end of the trigger wire pusher 180. For example, the opening at the distal end of the trigger wire pusher 180 may be sized to correspond to an outer diameter of the inner handle 160, while the opening at the proximal end of the trigger wire pusher may be sized to correspond to an outer diameter of the inner cannula 110, which may be smaller than the outer diameter of the inner handle. The trigger wire pusher 180 may be disposed at least partially within the lumen 154 of the handle 150. The trigger wire pusher 180 may extend through the proximal end opening of the handle 150 such that the proximal end of the trigger wire pusher is disposed outside and proximal of the handle as shown in FIGS. 4-5. Additionally, or alternatively, the trigger wire pusher 180 may be longitudinally movable relative to the handle 150. For example, the trigger wire pusher 180 may be retracted distally into the handle from a first position shown in FIG. 4 to a second position shown in FIG. 5. This may enable retraction of a trigger wire as further described below.

The inner handle 160 may be configured as a tubular member having a proximal end 162, a distal end 164, and a lumen extending longitudinally therein. The proximal end 162 may be flared as shown in FIGS. 4-5. The inner handle 160 may be disposed within the lumen 154 of the handle 150 (e.g., within the proximal compartment). The inner handle 160 may be fixed relative to the handle 150 as further described below. The inner handle 160 may be disposed at least partially within the lumen of the trigger wire pusher. The inner handle 160 may extend through the distal end opening of the trigger wire pusher 180 so that the distal end 164 of the inner handle 160 is disposed outside and distal of the trigger wire pusher as shown in FIGS. 4-5. In this manner, the distal end 164 of the inner handle 160 may protrude from the distal opening of the trigger wire pusher 180. The diameter of the opening at the distal end of the trigger wire pusher 180 is at least as large as the outer diameter of the distal end 164 of the inner handle 160. Upon retraction of the trigger wire pusher 180 into the handle 150 as described above, the trigger wire pusher may move axially along a portion of the length of the inner handle 160. However, the inner handle 160 may be prevented from exiting the trigger wire pusher 180 completely because of the flared proximal end 162. The flared proximal end 162 may have a diameter greater than the diameter of the openings at both the proximal end and the distal end of the trigger wire pusher 180. Additionally, or alternatively, the length of the inner handle 160 may be greater than that of the trigger wire pusher 180. Therefore, upon sufficient retraction of the trigger wire pusher 180 relative to the inner handle 160, the proximal end of the inner handle may contact the end wall at the proximal end of the trigger wire pusher while a portion of the distal end 164 of the inner handle 160 still protrudes from the distal end of the trigger wire pusher 180.

The trigger wire knob 170 may be configured as a ring that is disposed about the outer surface of the distal end 164 of inner handle 160 as shown in FIG. 2. This combined structure (e.g., the trigger wire knob 170 and the inner handle 160) may be disposed within the lumen 154 of the handle 150. In this manner, the trigger wire knob 170 may be disposed within the lumen 154 of the handle 150 and in an annular space between the inner handle 160 and the handle 150 as shown in FIGS. 4-5. The inner diameter of the handle 150 (e.g., the diameter of the lumen 154) is at least as large as the outer diameter of the trigger wire pusher 180.

The trigger wire knob 170 may be movable longitudinally relative to the handle 150 and/or the inner handle 160. For example, upon retraction of the trigger wire pusher 180 into the handle 150, the distal end of the trigger wire pusher may abut the trigger wire knob 170 to move the trigger wire knob distally within the lumen 154 relative to the handle 150 and the inner handle 160 from a first position as shown in FIG. 4 to a second position as shown in FIG. 5.

The proximal end of the trigger wire pusher 180 may extend outside the proximal end of the handle 150. The distal end 164 of the inner handle 160 may be secured inside the handle 150. For example, the distal end 164 of the inner handle may be attached and/or abut the proximal end of the divider 155 as shown in FIGS. 4-5. To that end, the divider 155 may include a recess configured to receive the distal end of the inner handle 160 as shown in FIGS. 4-5. The inner handle 160 may remain stationary with respect to the handle 150. For example, upon retraction of the trigger wire pusher 180 relative to the handle 150, the inner handle 160 may not move relative to the handle 150.

As can be seen in FIGS. 4-5, the tension mechanism may include an actuating mechanism 112, a safety mechanism 114, a spring knob 120, a back disc 130, and a torsion spring 140. The spring knob 120 may be configured as a tubular member having a proximal end, a distal end, and a lumen extending longitudinally therein. In one example, the spring knob 120 may be configured as a hollow cylinder. The spring knob 120 may include a proximal portion 122 with a reduced outer diameter. The proximal portion 122 of the spring knob 120 may be received within the lumen 154 of the handle 150 (e.g., within the distal compartment). Additionally, or alternatively, the proximal portion 122 of the spring knob 120 may be positioned near and/or about the divider 155.

The torsion spring 140 may be disposed about the spring knob 120. For example, the torsion spring 140 may be disposed about the proximal portion 122 of the spring knob 120 as shown in FIGS. 4-5. The torsion spring may be configured as any type of resilient member. For example, the torsion spring 140 may be configured as a wire (e.g., a substantially flat wire) having a first end and a second end. The wire may be rolled or coiled about the proximal portion 122 of the spring knob 120. The first end of the torsion spring 140 may be secured to the inside wall of the handle 150 near the distal end 156. In one embodiment, the first end of the torsion spring 140 has an exterior coil spring tongue 117 that is bent at an angle away from the torsion spring 140. The exterior coil spring tongue 117 fits into the spring slot 153 of the distal end of the handle 150. The second end of the torsion spring 140 may be secured to the proximal portion 122 of the spring knob 120. The ends of the torsion spring 140 may be secured using any suitable attachment mechanism including, for example, a screw, an adhesive, or a pin vice. In one embodiment, the second end of the torsion spring 140 has an interior coil spring tongue 119 that is bent at an angle away from the torsion spring 140. The interior coil spring tongue 119 fits into the spring slot 151 of the distal end of the spring knob 120. The spring knob 120 may be rotated relative to the handle 150 to tighten the torsion spring 140 (e.g., by winding the torsion spring around the spring knob). The torsion spring 140 may be tightened until the torsion spring 140 has a desired tension. The spring knob 120 may be secured relative to the handle 150 (e.g., to prevent rotation of the spring knob relative to the handle) with an actuating mechanism 112. The actuating mechanism 112 can be a pin or a spring-release mechanism. The actuating mechanism 112 can have a safety mechanism 114 (e.g., a locking mechanism) to inhibit unintentional actuation of the actuating mechanism 112.

The back disc 130 may be attached to the distal end 158 of the handle 150 as shown in FIGS. 4-5. In one embodiment, the back disc 130 has two holes 121. In this embodiment, the distal end of the handle 150 similarly contains two threaded holes 123 that correspond with the two holes 121 in the back disc 130. Two fasteners 127 can be used to secure the back disc 130 to the distal end of the handle 150. The back disc 130 may include an opening therethrough. The spring knob 120 may be disposed within the opening in the back disc 130. The back disc 130 may serve to prevent the longitudinal motion of the torsion spring 140 (e.g., by capturing the torsion spring within the distal compartment of the handle 150) thereby preventing the torsion spring from unraveling. The back disc 130 and the handle 150 can be formed separately or can be a unitary component (e.g., as part of an injection molded handle).

The inner cannula 110 extends longitudinally through the length of the deployment handle as shown in FIGS. 3-5. The inner cannula 110 may be disposed within each of the handle 150, the inner handle 160, the trigger wire knob 170, the trigger wire pusher 180, the spring knob 120, the torsion spring 140, and the back disc 130 as shown in FIGS. 4-5. The inner cannula 110 may be secured (e.g., fixed) to the spring knob 120. The inner cannula may be rotatable relative to the handle 150, the inner handle 160, the trigger wire knob 170, the trigger wire pusher 180, and/or the back disc 130.

FIG. 6 shows one example of a stent graft attached to a delivery device. The delivery device may have any suitable configuration. The handle 100 described herein may be configured for use with a delivery device that uses rotation of a cannula (e.g., the inner cannula 110) to release at least a portion of the stent graft. Suitable delivery devices may include, for example, any of those described in U.S. patent application Ser. No. 13/796,395, filed Mar. 12, 2013, and Ser. No. 13/669,145, filed Nov. 5, 2012, each of which is incorporated herein by reference in its entirety.

The stent graft may be positioned about the inner cannula 110 near the proximal end of the delivery device (e.g., near a tip of the delivery device). A trigger wire 194 may be attached to the stent graft as shown in FIG. 6 to maintain at least a portion of the stent graft in a reduced diameter configuration. The trigger wire 194 may run distally along the delivery device and through the trigger wire pusher 180 and the inner handle 160 as shown in FIGS. 4-5. A distal end of the trigger wire 194 may be secured to the trigger wire knob 170 as shown in FIGS. 4-5. The trigger wire 194 may secure at least a portion of the stent graft to the delivery device to prevent deployment of the stent graft before it has been placed at its intended location.

FIG. 6 illustrates the proximal end of the delivery device 600. As discussed above, a portion (e.g., the distal end) of the stent graft 650 is secured to the delivery device 600 by the trigger wire 194. At the proximal end of the stent graft 650, the top stent 640 includes a number of apices, which may be secured to the delivery device to retain the top stent in a reduced diameter configuration. For example, one or more suture loops 630 may be engaged with the top stent and a coiled member 620 at the distal end of the delivery device tip 610 as shown in FIG. 6. Further details of a suitable engagement mechanism are described in U.S. patent application Ser. No. 13/796,395, filed Mar. 12, 2013, the disclosure of which is hereby incorporated by reference in its entirety.

FIGS. 4-5 illustrate the steps for deployment of the stent graft 650 from the delivery device 600 using the deployment handle 100. In operation, a valve 190 and a sheath 192 are withdrawn together in a distal direction to expose the stent graft. At least a portion of the stent graft may remain in the reduced diameter configuration even after retraction of the sheath 192 (e.g., by engagement with the trigger wire 194, the coil member 620, or another engaging member of the delivery device 600). Upon retraction of the sheath 192, the valve 190 may be brought into abutting contact with the trigger wire pusher 180 as shown in FIG. 4. Further retraction of the valve 190 may cause retraction of the trigger wire pusher 180 into the handle 150. The distal end of the trigger wire pusher 180 may be in abutting contact with the trigger wire knob 170 so that retraction of the trigger wire pusher 180 into the handle causes the trigger wire knob 170 to move longitudinally relative to the handle 150 in a distal direction. The inner handle 160 may remain stationary relative to the handle 150 as described above. In this manner, the inner handle 160 may provide support for the trigger wire pusher 180 and/or the trigger wire knob 170 during longitudinal movement thereof relative to the handle. The inner cannula 110 may be fixed longitudinally relative to the handle 150 (e.g., by being secured to the spring knob 120). In this manner, longitudinal movement of the trigger wire knob 170 relative to the handle 150 may cause a corresponding longitudinal movement of the trigger wire knob relative to the inner cannula. The trigger wire 194 may be attached to the trigger wire knob as described above. Longitudinal movement of the trigger wire knob 170 relative to the inner cannula 110 may pull or retract the trigger wire 194 distally relative to the inner cannula. In this manner, the trigger wire 194 may be pulled out of engagement with the stent graft to enable expansion of at least a portion of the stent graft that had been retained by the trigger wire. The configuration of the handle may enable retraction of the sheath and release of the trigger wire using a single pulling action. This may reduce the number of steps performed by a clinician to deploy the stent graft.

An actuating mechanism may be actuated to release the spring knob 120 to enable rotation of the spring knob relative to the handle 150. FIGS. 9A-9B and FIGS. 10A-10B describe two such embodiments. Upon releasing the spring knob 120, the tension of the torsion spring 140 may cause the spring knob 120 to rotate relative to the handle 150. In other words, the torsion spring 140 may unwind causing rotation of the spring knob 120 relative to the handle 150. The spring knob 120 may be secured to the inner cannula as described above. Rotation of the spring knob 120 relative to the handle 150 may cause a corresponding rotation of the inner cannula 110 relative to the handle 150. Such rotation of the inner cannula 110 may release the stent graft from the delivery device. For example, the rotation of the inner cannula 110 may cause a corresponding rotation of the coiled member 620 that sits at distal end of the delivery device tip 610. Rotation of the coiled member 620 may cause the suture loops 630 on the apices of the top stent 640 to travel longitudinally in a distal direction until the suture loops 630 are no longer engaged with the coiled member 620 and the top stent 640 is released. The number of rotations of the spring knob 120 and the inner cannula 110 caused by the torsion spring 140 may correspond to the number of turns of the coiled member 620 which may be required to release the top stent 640 from the coiled member.

In another example, the delivery device 600 may include an engaging member disposed about the inner cannula and engaged with the tip 610. For example, the engaging member may be threaded into the tip 610. The engaging member may engage at least a portion of the stent graft. For example, the engaging member may include one or more projections extending outward away from the inner cannula and engaging the stent graft. The proximal stent of the stent graft may be captured between the projections of the engaging member and the tip 610 to retain the proximal stent in a reduced diameter configuration. The inner cannula may be rotatable within the engaging member. Upon rotation of the inner cannula (e.g., by actuation of the deployment handle 100 as described above), the tip 610 may rotate relative to the engaging member. This may cause the engaging member to unthread from the tip 610, which may cause the engaging member and the tip to move longitudinally away from one another to release the proximal stent.

In any of the embodiments described herein, the deployment handle may aid in deploying the stent graft. For example, using the torsion spring 140 to rotate the inner cannula 110 may reduce the effort exerted by a clinician (e.g., to manually rotate the inner cannula) to manipulate the delivery device. Additionally, or alternatively, using the torsion spring 140 may prevent errors by ensuring that the cannula is rotated in the correct direction. Additionally, or alternatively, the torsion spring 140 may enable quicker completion of the deployment procedure without compromising control.

Figure 7:
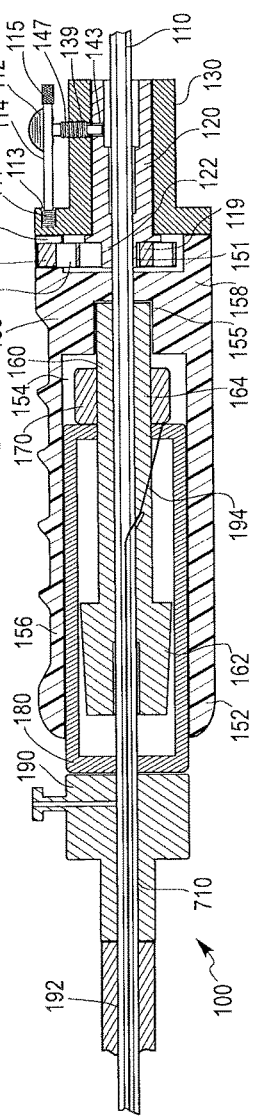
FIG. 7 illustrates a side view of another embodiment of a quick release deployment handle of a delivery device.
Figure 8:
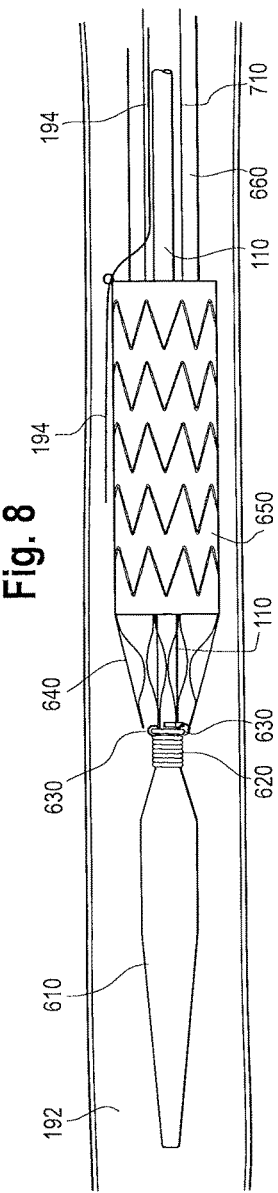
FIG. 8 illustrates a side view of the proximal end of the delivery device of FIG. 7 with a prosthesis loaded thereon.

FIGS. 7-8 illustrate another embodiment of a deployment handle 700, which may be configured as a quick release deployment handle. The configuration of the deployment handle 700 is substantially the same as the deployment handle 100 of FIGS. 1-6 except as described below. The deployment handle 700 may be configured for a delivery device including an outer cannula 710. The inner cannula 110 may be disposed within the outer cannula 710. The outer cannula 710 may extend longitudinally within each of the handle 150, the inner handle 160, the trigger wire knob 170, and the trigger wire pusher 180 as shown in FIG. 7. The outer cannula 710 may be attached to the spring knob 120. The inner cannula 110 may be capable of moving independently of the spring knob 120. At least a portion of the stent graft (e.g., the proximal stent) may be engaged with the outer cannula 710 rather than the inner cannula 110. For example, the coiled member 620 may be secured to the outer cannula 710.

In operation, the deployment handle 700 operates in substantially the same way as the deployment handle 100 of FIGS. 1-6. For example, the valve 190 may be retracted a sufficient distance to release the trigger wire 194 as described above. The actuating mechanism 112 may be actuated to release the spring knob 120 to enable rotation of the spring knob relative to the handle 150. When the actuating mechanism 112 is actuated and the spring knob 120 rotates, the inner cannula 110 may remain stationary relative to the handle while the outer cannula 710 rotates relative to the handle. Rotation of the outer cannula 710 may release at least a portion of the stent graft to enable expansion thereof. For example, rotation of the outer cannula 710 may cause rotation of the coiled member 620 as described above to release the proximal stent of the stent graft.

In another example, the proximal end of the outer cannula 710 may be threaded into the tip 610 of the delivery device. The delivery device may include an engaging member extending from the outer cannula 710 and engaging a portion of the stent graft. For example, the proximal stent of the stent graft may be captured between the engaging member and the tip 610. Rotation of the outer cannula 710 relative to the tip 610, which may be fixedly attached to the inner cannula 110, may cause the outer cannula to unthread from the tip. This may cause the tip 610 and the outer cannula 710 to move longitudinally away from one another. Such longitudinal movement may release the engaged portion of the stent graft (e.g., the proximal stent).

Turning now to FIGS. 9A-9B and 10A-10B, examples of safety locking mechanisms are illustrated. As previously mentioned, a safety locking mechanism may be provided on the quick release deployment handle to prevent unintentional rotation of inner cannula 110. It is desirable to prevent unintentional rotation of inner cannula 110 to preclude premature deployment of the stent graft, including, but not limited to the proximal stent of the stent graft.

As shown in FIGS. 9A and 9B, a hole 113 having internal threads is located in back disc 130. In one example, hole 113 may be located between holes 121 in back disc 130, although hole 113 may be positioned in other locations on back disc 130. A safety mechanism 114, which, in one example, may be rod shaped or otherwise linear may include a threaded portion 111 at its proximal end and a gripping portion 115 at its distal end. The distal gripping portion 115 may include a roughened gripping surface or be shaped so as to provide a convenient gripping shape and surface for the user. As shown in FIG. 9A, the proximal threaded portion 111 of the safety mechanism 114 is inserted into hole 113 so that threaded portion 111 is engaged with the internal threads of hole 113.

When safety mechanism 114 is engaged with hole 113 as illustrated in FIG. 9A, it preferably prevents rotation of actuating mechanism 112. Actuating mechanism 112 can be of various shapes and configurations, and in one example, may be in the form of a wing nut having a widened top portion and a rod or pin extending therefrom. The pin portion of this actuating mechanism 112 may include threads 147 which engage the inner threads of hole 141 formed in the distal end of the handle. In one example, the actuating mechanism 112, and more specifically, the base of the pin below threads 147, exerts pressure upon inner cannula 110 or otherwise is frictionally engaged with inner cannula 110 such that when actuating mechanism 112 is threadly engaged in hole 141, rotation of inner cannula 110 is prevented. In another example, in addition to or in combination with the above-mentioned frictional engagement, inner cannula 110 may have an indentation, socket or other structure that mates with or engages with the base of the pin of actuating mechanism 112 to prevent rotation of inner cannula 110 when actuating mechanism is threaded in hole 141.

At least a portion of the safety mechanism 114 is adjacent to, abuts and/or extends across at least one side of the widened top portion of the actuating mechanism 112, thus preventing rotation of the actuating mechanism 112. As shown in FIG. 9B, safety mechanism 114 may be rotated or "unscrewed" from threaded hole 113. This may be accomplished, for example, by the user gripping distal portion 115 of the safety mechanism 114 and rotating it until it is removed from threaded hole 113. With safety mechanism 114 removed as shown in FIG. 9B, the actuating mechanism 112 may then be rotated by the user, such as by gripping the widened top portion and rotating it (illustrated by the arrows as counter-clockwise rotation) which causes the threaded portion 147 to unscrew from threaded hole 141. With actuating mechanism 112 removed, inner cannula 110 may now be able to rotate, thus allowing release of the stent graft, including, but not limited to the proximal stent of the stent graft.

FIGS. 10A and 10B illustrate an alternative example of a safety locking mechanism on the quick release deployment handle to prevent unintentional rotation of inner cannula 110. As shown there, the distal end of the handle includes a user-actuated safety mechanism 125, which may be in the form of a sliding switch, lever, button or the like. In this example, the sliding switch 125 may slide longitudinally in a channel 145. As shown in FIG. 10A, the sliding switch 125 is located in the distal most portion of channel 145, such that a distal end 129 of the sliding switch 125 slides above and/or over a top portion of a spring 137. Spring 137 can be best seen in FIG. 10B as having a pin 133 running through the spring 137. The top end 135 of pin 133 may be covered by the distal end 129 of sliding switch 125 when the switch is positioned in the distal end of channel 145, which compresses the spring 137 into channel 143 formed in the distal end of the handle. As a result, the compression of the spring 137 creates downward pressure upon inner cannula 110, thus preventing rotation of the inner cannula 110. When the sliding switch 125 is moved in a proximal direction by the user, as illustrated by the arrow in FIG. 10A, the distal end 129 of sliding switch 125 moves proximally so that it is no longer covering the top end 135 of spring 137 and pin 133. The spring therefore expands through hole 141 formed in the distal end of the handle to its natural and uncompressed state such that the spring 137 and pin 133 is no longer frictionally engaged with nor is it exerting pressure upon inner cannula 110. As such, inner cannula 110 may now be able to rotate thus allowing release of the stent graft, including, but not limited to the proximal stent of the stent graft as previously described herein.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. A stent graft delivery system for a stent graft comprising:
 a delivery device having an inner cannula having a proximal end and a distal end;
 a stent graft carried on the proximal end of the inner cannula;
 a deployment handle comprising,
  a tubular handle having a proximal end and a distal end and a handle lumen extending longitudinally therebetween, wherein at least a portion of the distal end of inner cannula extends longitudinally through the handle lumen;
  a torsion spring proximal the distal end of the inner cannula, the torsion spring configured to impart axial rotation of the inner cannula relative to the handle;
  an actuation mechanism positioned at the distal end of the handle, the actuation mechanism having a first position in which the actuation mechanism is engaged with the inner cannula to prevent axial rotation of the inner cannula and a second position in which the actuation mechanism is an disengaged from the inner cannula to permit axial rotation of the inner cannula relative to the handle;
  wherein the axial rotation of the inner cannula permits release of at least a portion of the stent graft from the delivery device.

2. The stent graft delivery system of claim 1 wherein the torsion spring comprises a coiled element.

3. The stent graft delivery system of claim 1 wherein the actuation mechanism comprises at least one of a pin, rod, wing nut, screw, and spring.

4. The stent graft delivery system of claim 1 wherein the actuation mechanism further includes a safety mechanism preventing the actuation mechanism from inadvertently disengaging from the inner cannula to prevent inadvertent axial rotation of the inner cannula.

5. The stent graft delivery system of claim 4 wherein the safety mechanism comprises a linear member releaseably engageable with the distal end of the handle, the safety mechanism configured to prevent inadvertent rotation of actuation mechanism.

6. The stent graft delivery system of claim 1 wherein the torsion spring is axially rotated relative to the handle to impart tension in the torsion spring.

7. The stent graft delivery system of claim 6 wherein tension in the torsion spring is maintained when the actuation mechanism is in the first position engaged with the inner cannula.

8. The stent graft delivery system of claim 7 further comprising a slideable lever having a first position which maintains the actuation mechanism in its first position engaged with the inner cannula thereby maintaining the tension in the tension mechanism.

9. The stent graft delivery system of claim 8 wherein the slideable lever is moveable to a second position, and wherein movement of the lever to the second position operable to release tension in the tension mechanism, resulting in axial rotation of inner cannula.

10. The stent graft delivery system of claim 1 further comprising an outer cannula disposed about an outer surface of the inner cannula, wherein the outer cannula is axially rotatable relative to the inner cannula.

11. The stent graft delivery system of claim 1 wherein the handle further comprises a trigger wire pusher slideably disposed at least partially within the lumen of the handle, the trigger wire pusher having a proximal end, a distal end, and a lumen extending between the proximal and distal ends.

12. The stent graft delivery system of claim 11 further comprising a trigger wire knob disposed distally of the distal end of the trigger wire pusher, wherein the trigger wire knob is longitudinally slideable within the lumen of handle between a first proximal position and a second distal position; and at least one trigger wire having a proximal end attached to stent graft and a distal end attached to the trigger wire knob.

13. The stent graft delivery system of claim 12 wherein movement of the trigger wire knob from the first position to the second position moves the trigger wire distally.

14. The stent graft delivery system of claim 12 wherein the proximal end of the trigger wire disengages from stent graft when the trigger wire knob is in the second distal position, thereby releasing at least a portion of stent graft from the delivery device.

* * * * *